United States Patent [19]
Alexander et al.

[11] Patent Number: 5,243,993
[45] Date of Patent: Sep. 14, 1993

[54] APPARATUS AND METHOD FOR MEASURING HEART RATE

[75] Inventors: Donald J. Alexander, Milwaukee, Wis.; Allen J. Fuller, Naperville; William H. Englehardt, Wood Dale, both of Ill.; Douglas B. Macdonald, Des Plaines; Olgerts J. Svilans, Chicago, both of Ill.; Robert A. Bonner, Lincolnwood, Ill.

[73] Assignee: Life Fitness, Franklin Park, Ill.

[21] Appl. No.: 722,800

[22] Filed: Jun. 28, 1991

[51] Int. Cl.$^5$ .............................. A61B 5/04
[52] U.S. Cl. .................. 128/707; 128/706; 128/704; 128/708
[58] Field of Search ............... 128/695, 696, 698, 700, 128/702, 703, 704, 706, 707, 708, 715, 713

[56] References Cited

U.S. PATENT DOCUMENTS

| | | | |
|---|---|---|---|
| 4,211,237 | 7/1980 | Nagel | 128/698 |
| 4,244,021 | 1/1981 | Chiles, III | 364/413 |
| 4,248,244 | 2/1981 | Charnitski et al. | 128/706 |
| 4,281,663 | 8/1981 | Pringle | 128/689 |
| 4,319,581 | 3/1982 | Cutter | 128/707 |
| 4,403,184 | 9/1983 | Witt et al. | 128/695 |
| 4,898,182 | 2/1990 | Hawkins et al. | 128/707 |
| 4,979,110 | 12/1990 | Albrecht et al. | 128/700 |
| 5,146,414 | 9/1992 | McKown et al. | 128/713 |

FOREIGN PATENT DOCUMENTS 2165352  9/1984  United Kingdom.

OTHER PUBLICATIONS

Article—Application of Correlation Analysis to the Detection of Periodic Signals in Noise by Y. W. Lee et al., Proceedings of the I.R.E., 1950, pp. 1165-1171.
Article—Spectral Analysis of Electrocardiogram Signals of the Isolated Guinea Pig Heart for the Detection of Arrhythmias by F. I. Chaudhry et al., J. Biomed. Eng., 1982, vol. 4, p. 287, Oct. 1982.
Article—Digital Signal Processing Applications Using the ADSP-2100, Family Applications Handbook, vols. 1, 2, 3 and 4.

Primary Examiner—William E. Kamm
Assistant Examiner—George Manuel
Attorney, Agent, or Firm—Jenner & Block

[57] ABSTRACT

An apparatus for measuring heart rate is provided which comprises a sensor for generating a signal which includes the biopotential signal produced by a heart. This signal is filtered, amplified and digitized. A microcomputer autocorrelates the digitized signal. A plurality of signal indication routines then scan the autocorrelated output for the presence of periodic signals. Each of the signal indication routines uses different search criteria, such as peak and waveform detection, and generates a candidate heart rate. An arbitrator then selects one of the candidate heart rates according to predetermined criteria. These criteria include the value of previously selected heart rates.

27 Claims, 8 Drawing Sheets

APPARATUS AND METHOD FOR MEASURING HEART RATE

FIELD OF THE INVENTION

The invention relates to the field of heart rate monitors, and in particular, to heart rate monitors used for measuring the heart rate of a person engaged in physical exercise.

BACKGROUND OF THE INVENTION

When the heart or another muscle contracts, the body generates a very low amplitude electric signal known as a biopotential signal. It is well known that this biopotential signal can be electronically detected on the surface of a person's skin. Because the heart expands and contracts in a regular rhythm, it generates a periodic biopotential signal. Thus, certain periodic voltage fluctuations on a person's skin correspond to heartbeat.

Devices for monitoring the heart rate of a human or animal are well known. Examples of these types of devices are described in U.S. Pat. Nos. 4,248,244; 4,540,001; and 4,898,182. Generally, most heart rate monitors use electrodes to sense voltage fluctuations on a person's skin. The signal thus sensed is then amplified and passed through a suitable filter for filtering out the biopotential signals unrelated to heart rate. The frequency of the residual signal is then determined and displayed as heart rate (in beats per minute).

Under certain ideal conditions, such as found in a hospital, the heart-related biopotential signal can be easily separated from other signals. During physical exercise, however, biopotential signals generated from the movement of muscles other than the heart tend to mask the heart's biopotential signal. Particularly troublesome are repetitive exercises, such as riding an exercise bike. In repetitive exercises, muscles tend to be exerted in a rhythmic or periodic fashion, thereby generating a periodic biopotential signal which cannot easily be distinguished from heart rate.

Equally problem prone is the interface between the human subject and the electrodes which are used to detect biopotential signals. In practice, persons exercising prefer to not be encumbered by the types of bracelet, harness or clip which are typically used to make contact with the electrodes. Ideally, the electrodes are placed on a handlebar or other location which the person touches as a matter of course while exercising. Under these conditions, however, the person is likely to remove his or her hands from time to time, thereby complicating efforts to accurately and continuously monitor heart rate.

One example of deficiencies in the prior art is provided by U.S. Pat. No. 4,248,244, issued to Charnitski et al. Charnitski teaches the use of electrodes which are connected to an electronic circuit for producing a burst of alternating electronic signal in response to biopotential impulses. The electronic circuit in turn is connected to a peak detector, which detects the peak amplitude of each burst of alternating signals and produces an electric pulse related in time thereto. A computer is used to measure the time between pulses and to selectively convert the measured times to a number representing heart rate. In practice, however, the arrangement disclosed Charnitski is unable to distinguish heart rate from other periodic muscular movements (such as pedaling a bicycle).

SUMMARY OF THE INVENTION

It is therefore an object of the present invention to provide an apparatus for measuring heart rate having an autocorrelator. The apparatus has a sensor which generates an input signal that includes the biopotential signal produced by a heart. The autocorrelator periodically generates an autocorrelation signal of the input signal over a predetermined time period. Signal indication logic is responsive to the autocorrelation and detects the presence of a periodic signal in the autocorrelation signal. The signal indication logic then generates a heart rate signal corresponding to the frequency of the periodic signal.

In one embodiment of the invention, the signal indication logic includes logic for detecting a peak in the autocorrelation signal which is in excess of a first threshold value, and a peak which is in excess of a second threshold value. In another embodiment, the signal indication logic includes logic for detecting a pulse in the autocorrelation signal which has a waveform characteristic of a heartbeat. In some cases, the autocorrelator generates the autocorrelation signal in the time domain.

It is another object of the invention to provide an apparatus for measuring heart rate having an arbitrator which selects a heart rate signal from a plurality of candidate output signals according to predetermined criteria. The apparatus includes a sensor which generates an input signal that includes the biopotential signal produced by a heart. The apparatus also includes signal processing means responsive to the input signal which detect the indication of periodic signals in the input signal. The signal processor generates a plurality of output signals corresponding to each of the frequencies of these periodic signals. These output signals are the candidate output signals from which the arbitrator selects the heart rate signal.

In one embodiment the signal processor includes logic for detecting a peak in the input signal which is in excess of a first threshold value, and detecting a peak in the input signal which is in excess of a second threshold value. In another embodiment, signal processor includes logic for detecting a pulse in the input signal which has a waveform characteristic of a heartbeat.

In yet another embodiment, the criteria used by the arbitrator include reasonableness criteria. In one case, the arbitrator includes memory for storing the value of the selected candidate output signal, and the reasonableness criteria include rejecting a candidate output signal if its value deviates from the previously selected candidate output signal by more than a predetermined amount. In another case, the arbitrator includes a device which measures the rate of work being performed by the subject whose heart rate is measured, and the reasonableness criteria include rejecting a candidate output signal if its value is not proportional to the rate of work being performed by the subject.

In yet another case, the reasonableness criteria including rejecting candidate output signal if its value falls outside of a predetermined range.

It is another object of the invention to provide apparatus for measuring heart rate of a human while exercising, having an autocorrelator and an arbitrator. The apparatus has a sensor which generates an input signal that includes the biopotential signal produced by a heart. The autocorrelator is responsive to the input signal for periodically generating an autocorrelation signal of the input signal over a predetermined time period. The apparatus also has a signal processor which is responsive to the autocorrelation signal for detecting the indication of periodic signals therein. The signal processor generates a plurality of output signals corresponding to the frequency of these periodic signals. The arbitrator is responsive to these output signals, and selects that one of the output signals which most likely represents true heart rate, according to predetermined criteria.

In one embodiment, the apparatus also has an analog-to-digital converter which generates a digital signal corresponding to the input signal. In some cases, the autocorrelator is a programmable digital signal processor. In other cases, the apparatus includes a low pass digital filter which filters the signal between the analog-to-digital converter and the autocorrelator.

In another embodiment, the apparatus has an adjustable gain amplifier which amplifies the input signal, and logic which adjusts the gain of the adjustable gain amplifier so that its output remains within a predetermined range.

In yet another embodiment, the signal processor includes logic for detecting a pulse in the autocorrelation signal which has a waveform characteristic of a heartbeat. In some cases, the digital signal processor also includes logic for detecting a peak in the autocorrelation signal which is in excess of the first threshold value, and a peak which is in excess of a second threshold value. In some cases, the digital signal processor is a programmable digital signal processor.

In another embodiment, the sensor also has a plurality of electrodes which sense the biopotential signal produced by the human's body when the electrodes are placed into contact with the human. In some cases, the sensor also has a circuit responsive to the electrodes which generates a hands on/off signal that indicates whether the electrodes are in contact with the human. In other cases, the autocorrelator discontinues processing the input signal if the hands on/off signal remains at zero for a predetermined amount of time. The autocorrelator does not continue processing the input signal again until the hands on/off signal resumes a value other than zero.

In another embodiment of the invention, the arbitrator's predetermined criteria include reasonableness criteria. In some cases the apparatus further comprises circuitry for generating a motion signal corresponding to the frequency of repetitive motions performed by the human while exercising. In these cases, the reasonableness criteria include rejecting an output signal whose value is a multiple of the value of the motion signal.

DETAILED DESCRIPTION OF THE INVENTION

Overview

Figure 1:
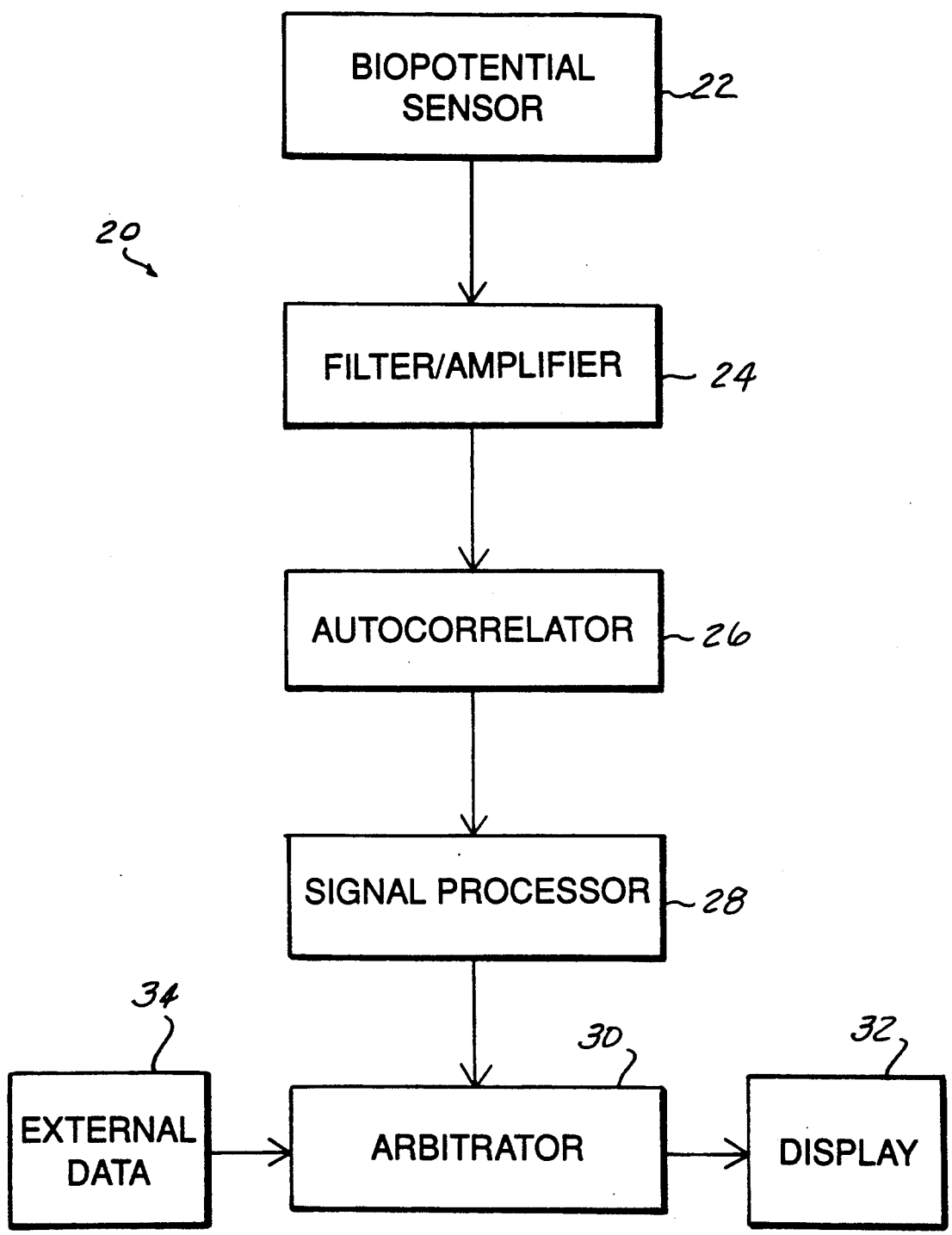
FIG. 1 is a block diagram of a generalized apparatus for measuring heart rate in accordance with the invention.

FIG. 1 is a block diagram of an apparatus 20 for measuring heart rate in accordance with the invention. Apparatus 20 comprises a biopotential sensor 22, a filter/amplifier stage 24, an autocorrelator 26, a signal indicator 28 and an arbitrator 30. When the biopotential sensor 22 is placed in contact with a human subject, it generates an electric signal corresponding to the biopotential signals generated by the human. Generally speaking, the human body produces these biopotential signals when muscles, including the heart, expand and contract. Thus, the electric signal generated by the biopotential sensor 22 includes biopotential signals corresponding to the beating of the subject's heart. The electric signal also includes noise and signals corresponding to other bodily functions. As described in greater detail below, the primary function of apparatus 20 is to determine heart rate from the noisy signal comprising all of the subject's biopotential signals.

The output of the biopotential sensor 22 is applied to the filter/amplifier 24, where it is filtered and amplified after which the output of the filter/amplifier 24 is fed into the autocorrelator 26, which generates a signal that represents autocorrelation of the output of the filter/amplifier 24. Autocorrelation algorithms are described in *Practical Approaches To Soeech Coding*, Panos E. Papamichalis, Prentice-Hall, Inc., Englewood Cliffs, New Jersey (1987). The output of the autocorrelator 26 is used as an input to the signal processor 28 which detects the presence of periodic signals in the output of the autocorrelator 26. The signal processor 28 generates a number of candidate signals, each of which corresponds to heart rate measured in beats per minute ("BPM"). To generate these signals, signal processor 28 employs several signal indicators for detecting the presence of a signal that could correspond to a heartbeat contained in the output of the autocorrelator 26. Each of these signal indicators (not shown in FIG. 1) employs a different technique, and generates one of the candidate signals.

The candidate signals are applied to the arbitrator 30, which uses predetermined criteria to decide which one of the candidate signals is most likely the subject's true heart rate. The heart rate selected by arbitrator 30 is displayed on display unit 32. Preferably, tho arbitrator 30 takes external data into account when selecting a heart rate. External data is supplied to the arbitrator 30 by an external data interface unit 34. The exact nature of the interface unit 34 depends on the environment in which the invention is practiced. For example, if the invention is applied in an exercise environment, the interface unit 34 can be a tachometer, ergometer or other device designed to measure the amount of work performed by the subject.

Hardware Configuration of the Preferred Embodiment

Figure 2:
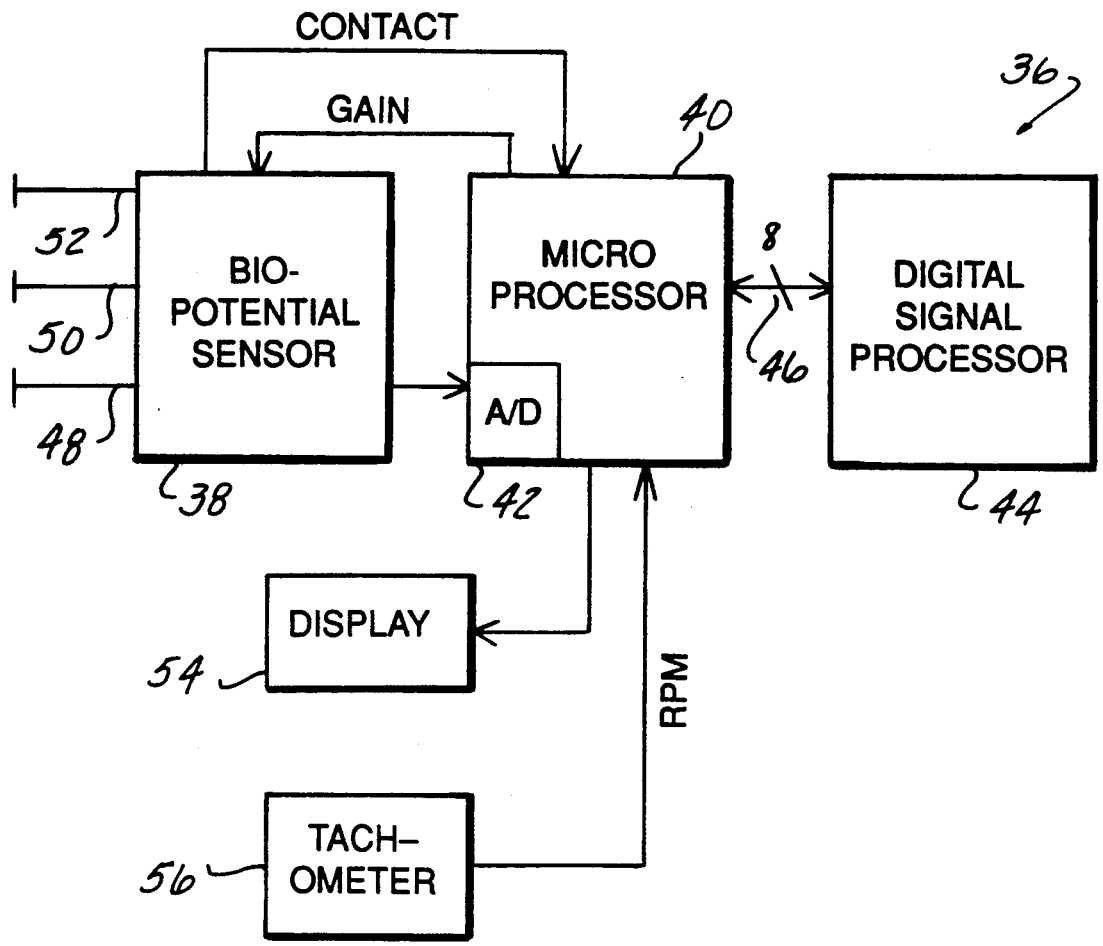
FIG. 2 is a block diagram of the preferred embodiment of the apparatus shown in FIG. 1.

FIG. 2 is a block diagram of a heart rate monitor 36 which embodies the generalized apparatus shown in FIG. 1 The monitor 36 includes a biopotential sensor 38, a microprocessor 40 which is electronically connected to the biopotential sensor 38 via an analog-to-digital convertor 42 ("A/D convertor"), and a digital signal processor 44, which is preferably an ADSP-2105 microcomputer by Analog Devices, of Norwood, Massachusetts, connected via an eight bit serial port interface 46 to the microprocessor 40. The biopotential sensor 38 includes three electrodes 48, 50 and 52. The biopotential sensor 38 and the accompanying electrodes 48, 50 and 52 are described below in greater detail. The microprocessor 40 is preferably a Motorola 68HC05, which is commercially available.

The biopotential sensor 38 is additionally coupled to microprocessor 40 by a CONTACT signal line and a GAIN signal line. The CONTACT signal provides an indication of whether a subject is in physical contact with the electrodes 48, 50 and 52. The GAIN signal provides a control value for controlling the gain of an adjustable gain amplifier which is included (but not shown) in the biopotential sensor 38. The operation of the GAIN signal is described below in connection with FIG. 5. Microprocessor 40 is additionally coupled to a display 54 and an ergometer 56. The display 54 is an LED or like display for displaying the true heart rate as computed by monitor 36. The ergometer 56 may include a tachometer or other device FIG. 3 for measuring the work and rate of work performed by the subject.

Figure 3:
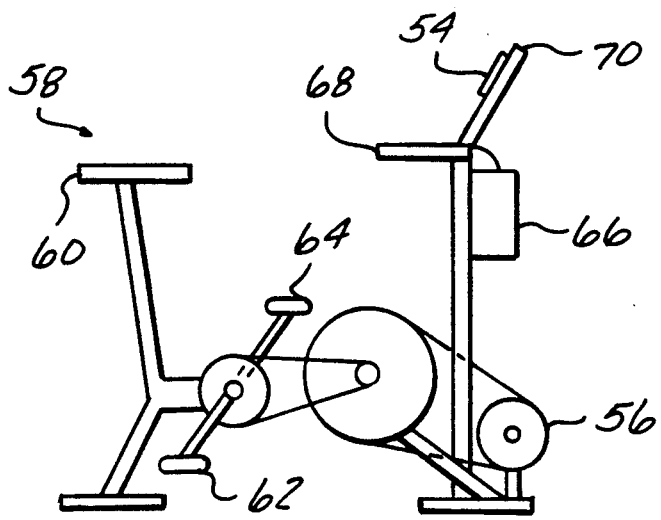
FIG. 3 is a side view of an exercise appliance which incorporates the apparatus of FIGS. 1 and 2.

FIG. 3 illustrates the exercise appliance 58 which, in this case, is a stationary bicycle, that includes a seat 60. The purpose of exercise appliance 58 is to provide the user a means of conveniently exercising. To this end, the user sitting on the seat 60 pedals the pedals 62 and 64 which are operatively connected to the ergometer 56. In this case the ergometer 56 is a tachometer which measures the revolutions per minute of the pedals 62 and 64. Other means for measuring the work and rate of work performed by the user are widely known and can be employed. As shown in FIG. 2, the tachometer 56 is operatively associated with microprocessor 40 for providing an RPM signal indicating the speed at which the pedals 62 and 64 are revolving. The exercise bicycle 58 also includes a housing 66, a handlebar 68 and the LED display 54 shown in FIG. 2. The biopotential sensor 38, the microprocessor 40, the A/D converter 42 and the digital signal processor 36 of FIG. 3 are contained (but not shown) in the housing 66. The electrodes 48, 50 and 52 are operatively disposed on the handlebar 68, as described below in greater detail. In practice, the control panel 70 also contains other displays and control buttons for enabling the subject to select a variety of operating modes available on exercise appliance 58. The exercise bicycle 58 is but one example of the applications to which the invention may be applied.

Figure 4A:
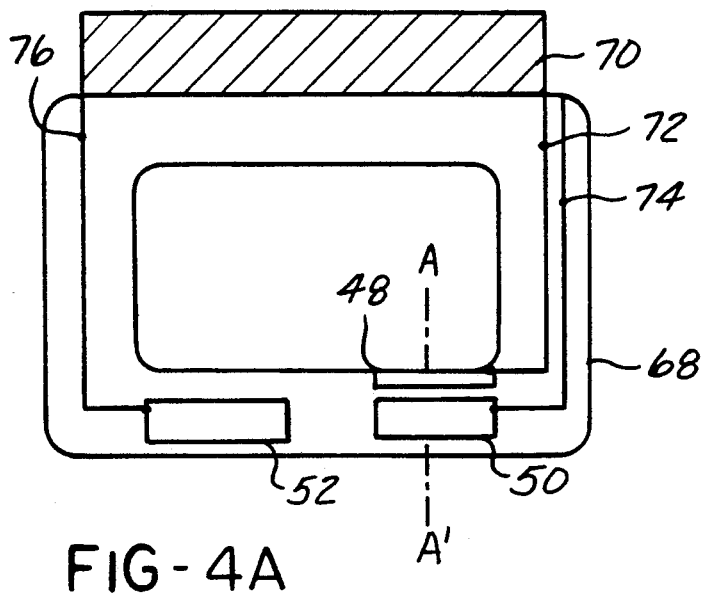
FIG. 4A is a top view of three electrodes mounted onto the handlebars of the exercise appliance shown in FIG. 3.
Figure 4B:
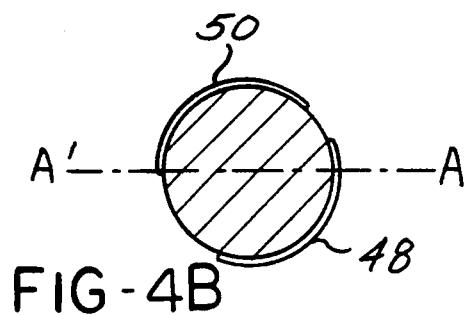
FIG. 4B is a sectional view of the electrodes and handlebars taken along the line A—A' shown in FIG. 4A.

FIG. 4A is a top view of the handlebar 68. FIG. 4B is a cross section view of handlebar 68 taken at the line segment A—A' As shown in FIGS. 4A and 4B, the handlebar 68 is a cylindrical member which is bent into a rectangular-shaped ring. The electrodes 48, 50 and 52 are preferably rectangular-shaped strips of conductive material, which are mounted upon the handlebar 68 so that their respective longitudinal edges are parallel with the handlebar 68. As shown in FIG. 4A, the electrodes 50 and 52 are positioned along the top side of the handlebar 68 so that they will come into direct physical contact with the palms of the user's right and left hand, respectively, when he grasps the handlebar 68 with both hands. As shown in FIG. 4B, the electrode 48 is juxtaposed with the electrode 50 on the opposing side of the handlebar 68. In this manner, when the user places his hands on handlebar 68, electrode 48 is placed in to contact with the fingers of the user's right hand. Each electrode 48, 50 and 52 is electrically coupled to the biopotential sensor 38 by a wire 72, 74 and 76, respectively. Other types of electrode and handlebar arrangements can also be employed.

Figure 5:
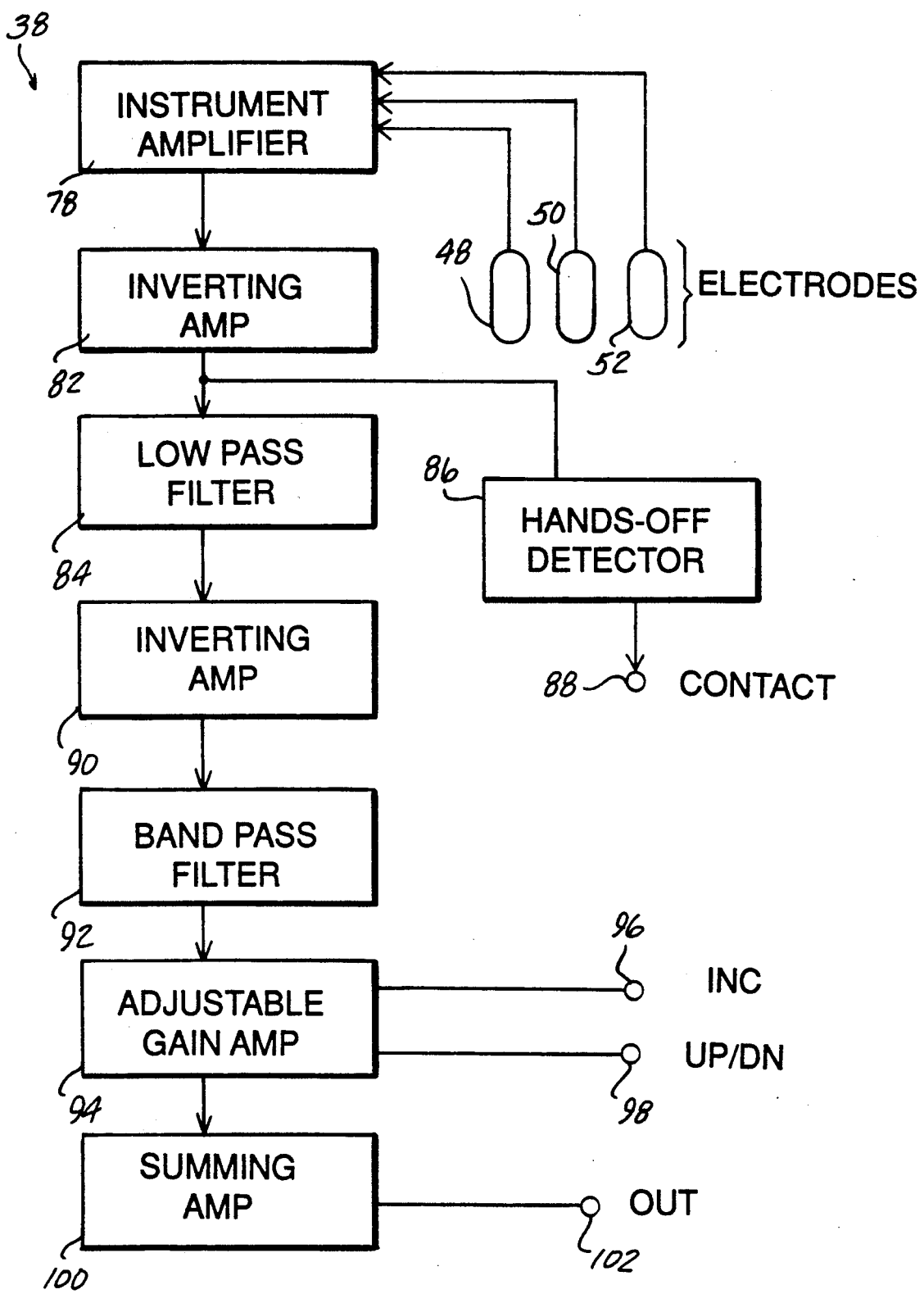
FIG. 5 is a block diagram of the biopotential sensor of the apparatus shown in FIG. 2.

FIG. 5 is a block diagram illustrating the biopotential sensor 38 in greater detail. When the user grasps the handlebar 68, his hands come into contact with the electrodes 48, 50 and 52 as described above. In this manner, an electric circuit is closed between electrodes 50 and 52 through the user's body, and a voltage potential (i.e., the biopotential) is created across the electrodes 50 and 52. The origin of this voltage potential is the bioelectric activity of the user's muscles, including the heart. The electrode 48 acts as a common mode reference. Each of the electrodes 48, 50 and 52 is electrically coupled to an instrument amplifier 78. The output of the instrument amplifier 78 is electronically coupled to an inverting amplifier 82. The output of the inverting amplifier 82 is electronically coupled to both a low pass filter 84 and a hands-off detector 86. The output of hand-off detector is the external signal CONTACT generated at a terminal 88. When the user removes his hands from the handlebar 68, the hands-off detector 86 causes the CONTACT signal to go to a low voltage (or logical "low") state on the terminal 88, and when the user places his hands on the handlebar 68, the hands-off detector 86 causes the CONTACT signal to be at a high voltage (or logical "high") state.

The output of the low pass filter 84 is applied to an inverting amplifier 90 and the output of the inverting amplifier 90 is input to a band pass filter 92. The output of the band pass filter 92 is electrically coupled to an adjustable gain amplifier 94. The adjustable gain amplifier is a conventional circuit which is responsive to a pair of external digital signals INC and UP/DN, which are applied to the adjustable gain amplifier 94 over a pair of terminals 96 and 98, respectively. The adjustable gain amplifier 94 operates so that when the UP/DN signal is at a logical high, the gain of the adjustable gain amplifier 94 is incremented by a predetermined amount each time the INC signal is strobed. Conversely, when the UP/DN signal is at a logical low state, the gain of the adjustable amplifier 94 is decremented by a predetermined amount each time the INC signal is strobed. For simplicity, the INC and UP/DN signals are show collectively as the GAIN signal in FIG. 2. The output of adjustable gain amplifier 94 is coupled to a summing amplifier 100 and the output of the summing amplifier 100 is made available at a terminal 102.

Figure 6:
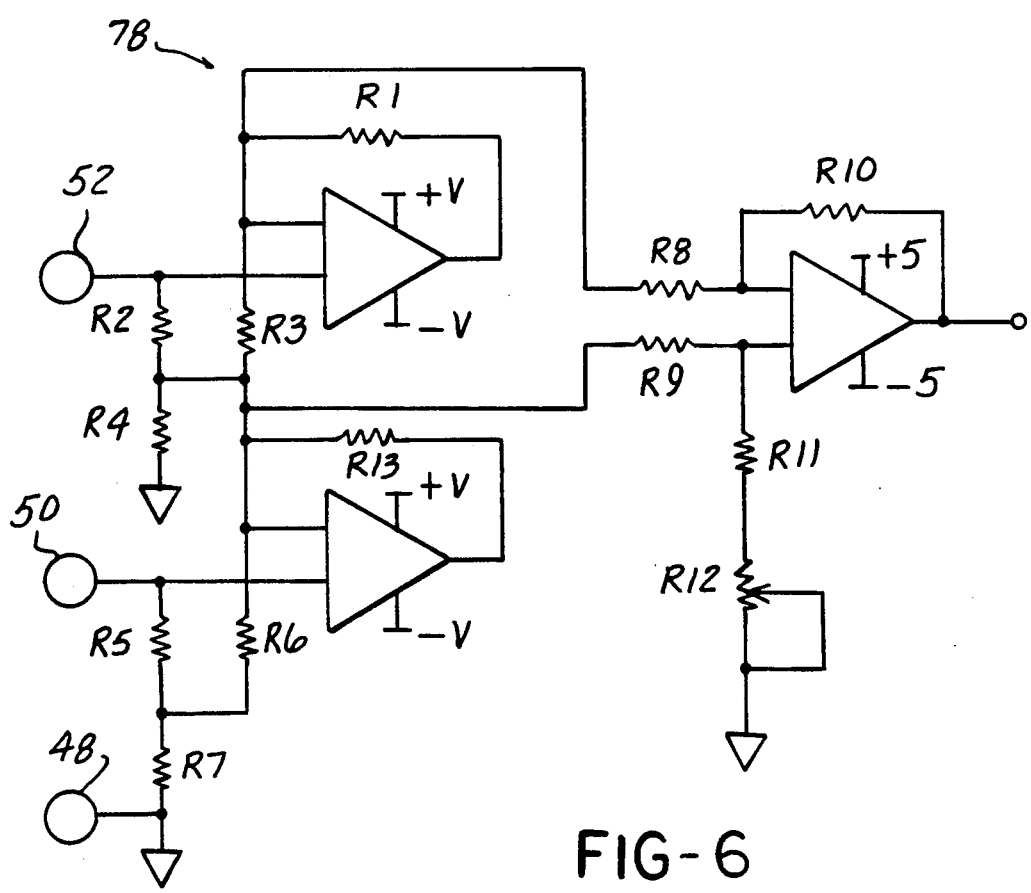
FIG. 6 is a schematic diagram of the electrodes and instrument amplifier of the biopotential sensor shown in FIG. 5.

Each of the foregoing components 78 through 100 are widely known and commercially available. Other widely-known methods of constructing biopotential sensor 38 are also available. Preferably, the instrument amplifier 78 will be of the type illustrated in FIG. 6. The hands-off detector 86 can be of the type shown in FIG. 7.

Software Confiouration of Preferred Embodiment

The operation of the monitor 36 may be understood by reference to the block diagram of FIG. 1. Each of the functions of the apparatus 20 is implemented in the monitor 36. Thus, the biopotential sensor 22, as shown in FIG. 1, is implemented in the biopotential sensor 38 and the electrodes 48, 50, 52. The filter/amplifier 24, as shown in FIG. 1, is also included in the biopotential sensor 38. Preferably, additional filtering is performed by the digital signal processor 44. The autocorrelator 26, the signal processor 28 and the arbitrator 30, as shown in FIG. 1, are implemented in the digital signal processor 44. The external data interface unit 34, as shown in FIG. 1, is implemented by the tachometer 56, and the display 32, as shown in FIG. 1, is implemented by the display 54.

In the preferred embodiment, the output of the biopotential sensor 38 is converted from an analog to digital signal by the A/D converter 42 and then used by the digital signal processor 44. The microprocessor 40 functions as an input/output interface between the A/D converter 42 and the digital signal processor 44.

Figures 7, 8:
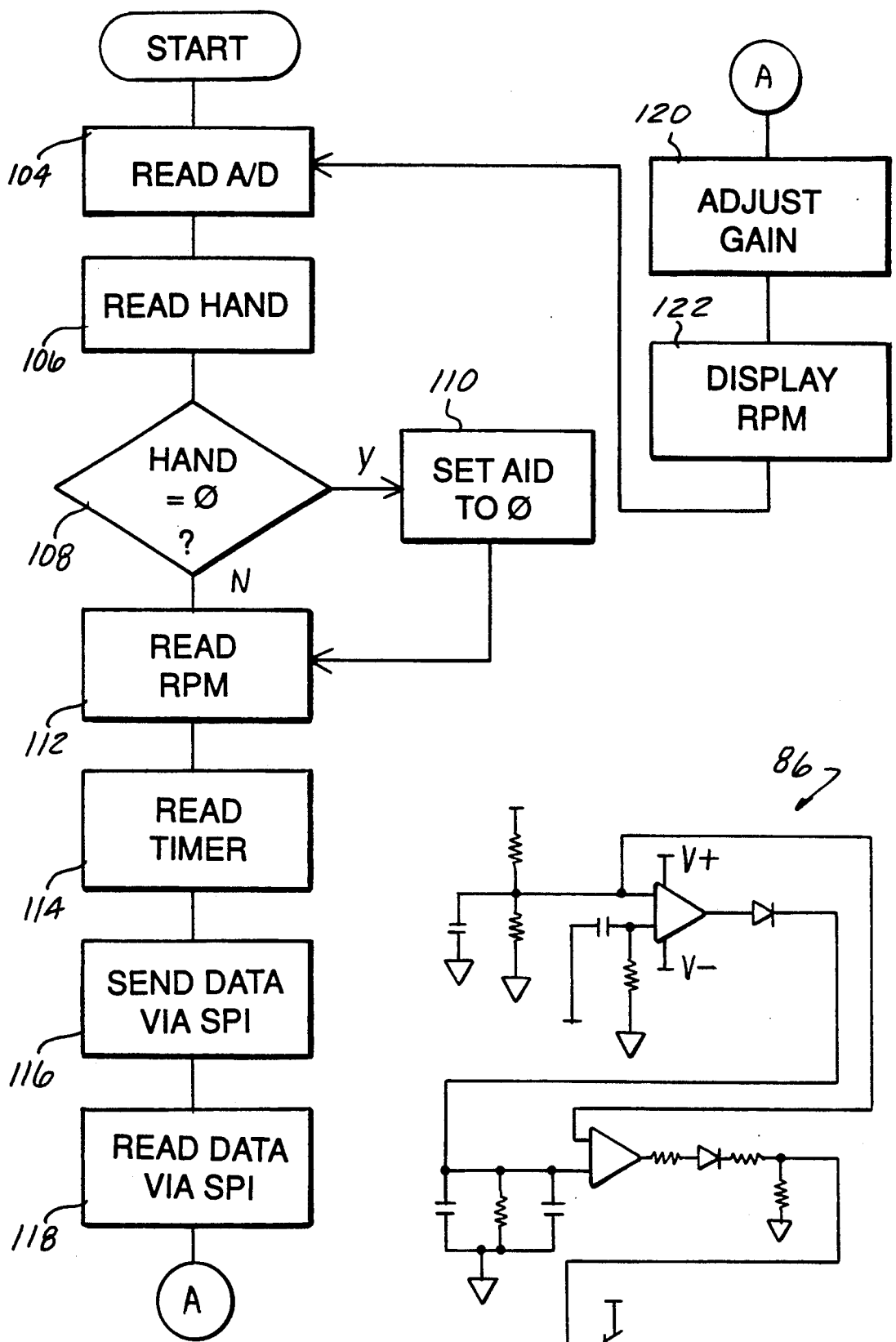
FIG. 7 is a schematic diagram of a hands-off detector circuit used in the biopotential sensor shown in FIG. 5.
FIG. 8 is a logic flow chart illustrating the operation of a microprocessor in the apparatus shown in FIG. 2.

FIG. 8 is a logical flow chart illustrating the operation of microprocessor 40. Beginning at a block 104, the microprocessor 40 stores the output of the A/D converter 42, thereby capturing a digital sample of the analog value of the output of the biopotential sensor 38. As described below, microprocessor 40 preferably samples the A/D converter output 42 every four milliseconds. For convenience, the operation performed at the block 104 is referred to as a "sample". Then, at a block 106, microprocessor 40 stores the status of the CONTACT signal. At a decision block 108, if the microprocessor 40 determines that the value of the CONTACT signal is zero (indicating that the user's hands are off the electrodes 48, 50 and 52), then control moves to a block 110. Otherwise, control moves to a block 112. At block 110, the microprocessor 40 sets the stored value of the A/D converter 42 to zero, and then moves to a block 112.

At the block 112, the microprocessor 40 stores the value of the RPM signal, which is generated by the tachometer 56. At a block 114, the microprocessor 40 stores the value of a timer not shown. The timer measures the amount of time which the user has been operating the exercise appliance 58. The timer is reset whenever the RPM signal has a zero value. Control then moves to a block 116 where the microprocessor 40 sends a data packet to the digital signal processor 44 via serial port interface 46.

Preferably, the data packet comprises the following eight bytes:
1. STX (startOof-data flag)
2. gain status
3. A/D sample data
4. RPM
5. elapsed time
6. hands on/off indication
7. checksum of the first six bytes
8. ACK or NAK The calculation of the checksum which is transmitted in byte six may be performed according to any one of numerous, widely-known techniques. Similarly, the communications protocol bytes STX, ACK and NAK can be provided in accordance with a conventional communication protocol. The hands on/off indication corresponds to the value of the CONTACT signal. The A/D sample data is the value of the stored output of the A/D converter 42. Gain status indicates the value of the gain command which has been most recently implemented.

At a block 118, the microprocessor 40 reads a data packet from a serial port interface buffer (not shown) of the digital signal processor 44. Preferably, the data packet read from the digital signal microprocessor 44 comprises the following eight bytes:
1. STX (start-of-data flag)
2. computed value of heart rate
3. gain command
4. zero
5. zero
6. zero
7. checksum of the first six bytes
8. ACK or NAK Control then moves to a block 120, where the microprocessor 40 operates to adjust the gain of the adjustable gain amplifier 94 in accordance with the gain command contained in the third byte of the data packet which the microprocessor 40 reads at the block 118. As indicated above, the adjustable gain amplifier 94 is a component of the biopotential sensor 38, and is responsive to the external digital signals INC and UP/DN (as shown in FIG. 5), which are collectively shown as the GAIN signal in FIG. 2. At a block 122, the microprocessor 40 displays on display 54 the value of the computed heart rate which is contained in byte two of the data packet read in the block 118.

Upon completion of step 122, control returns to the block 104, where the steps 104 through 122 are repeated. This sample cycle is repeated every four milliseconds. In this manner, the microprocessor 40 functions as an input/output interface between the digital signal processor and the biopotential sensor 38, the display 54 and the tachometer 56.

Figure 9:
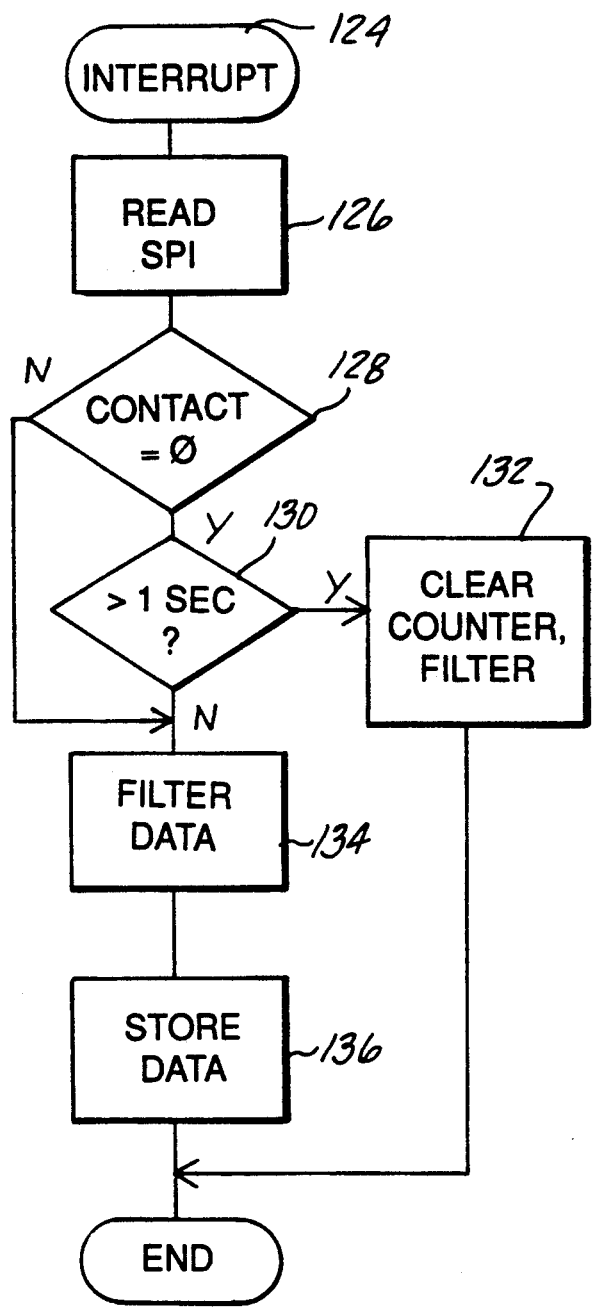
FIG. 9 is a logic flow chart illustrating the input/output operation of a digital signal processor of the apparatus shown in FIG. 2.
Figure 10:
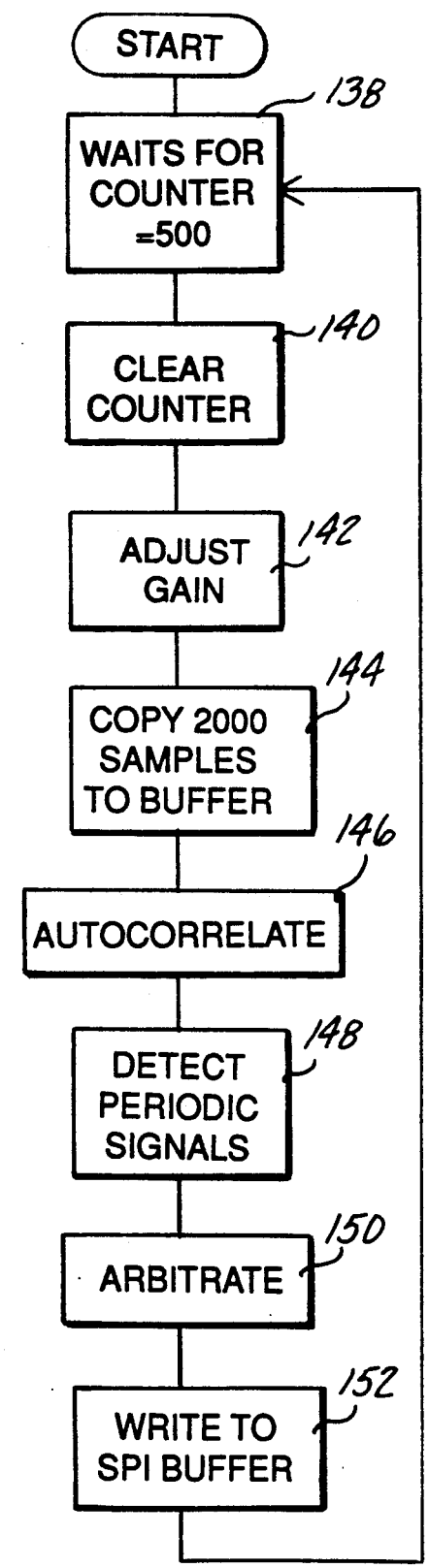
FIG. 10 is a logic flow chart illustrating the signal processing operation of the digital signal processor of the apparatus shown in FIG. 2.

The user's heart rate is computed by the digital signal processor 44, the operation of which is illustrated by the logic flow charts set forth in FIGS. 9 and 10. FIG. 9 illustrates an interrupt routine which is invoked when microprocessor 40 sends the data packet via the serial port interface 46 to digital signal processor 44. At an interrupt block 124, the digital signal processor 44 suspends its other processing activity as described below in connection with FIG. 10. Control then moves to a block 126, where the digital signal processor 44 reads the data packet sent by microprocessor 40. At decision block 128, microprocessor 40 determines whether the hands on/off indication, contained in byte six of the data packet and corresponding to the value of the CONTACT signal, is equal to zero.

If the hands on/off indication is equal to zero, control moves to a decision block 130. Otherwise control moves to a decision block 134. At the decision block 130, if the hands on/off indication has been zero for more than a predetermined time, preferably one second, then control moves to a block 132. Otherwise control continues to the block 134. The determination as to whether one second has elapsed is made by use of a timer (not shown) within the digital signal processor 44, which is reset whenever the value of the hands on/off indication goes to zero. At the block 132, the digital signal processor 44 clears a counter and a digital filter (not shown), the operation of which are discussed below. Control then moves from the block 132 to the block 134.

At the block 134, the digital signal processor 44 passes the incoming A/D sample data, contained in byte three of the data packet received from the microprocessor 40 at the block 126, through the above-mentioned digital filter. Preferably, the digital filter is a low-pass Bessel IIR digital filter, for which the center frequency is 10 Hz, the bandwidth is 20 Hz, the transition band is 50 Hz, and the stopband attenuation is approximately 50 Db at 70 Hz. Control then moves to a block 136 where the digital signal processor 44 stores the filtered A/D digital sample in a circular buffer. Preferably, the buffer has at least 2,500 data elements. For a four millisecond sample cycle, the buffer will hold A/D sample data taken over a 10 second period.

The operation of the digital signal processor 44 in determining heart rate is illustrated by the logic flow chart set forth in FIG. 10. As discussed above, a counter (not shown) is operatively associated with the digital signal processor 44 for counting the number of times A/D sample data is read into the circular buffer. At a block 138, the digital signal processor 44 waits for the counter to reach a predetermined value preferably, 500. In this case, 500 A/D samples represent data taken over a two second period. When the counter reaches the predetermined value, control moves to a block 140, where the counter is cleared. At a block 142, the contents of the circular buffer are inspected to find the peak value of A/D sample data. If the peak value indicates a voltage outside of a predetermined range (preferably, between 4.25 volts and 4.7 volts), the gain of the adjustable gain amplifier 94 is adjusted so that peak voltage falls within the predetermined range. This adjustment is accomplished by generating a gain adjustment command, which is discussed below in greater detail.

At a block 144, a predetermined number of samples (preferably, 2000) are copied from the circular buffer into a work buffer. The work buffer is preferably an array of 2000 data storage elements. At block a 146, an autocorrelation is performed on the contents of the work buffer. The autocorrelation is preferably implemented by computing the value of $R_k$ over k equal to 1 through N, where N is preferably 400, accordinq to the followinq formula:

$$R_k = \sum_{m=0}^{N-1-k} S_m \cdot S_{(m+k)}$$

where $S_m$ equals value of the A/D sample data in the $m^{th}$ element of the work buffer. The values of $R_k$ are stored in an autocorrelation output buffer, which is preferably an array of data storage elements R[0]through R[N]. Thus, $R_k$ is the value stored in the $k^{th}$ element of the autocorrelation output buffer. The block 146 represents the function performed by the autocorrelator 26 shown in FIG. 1.

At a block 148, the digital signal processor 44 then conducts a series of examinations of the contents of the autocorrelation output buffer. Each examination utilizes a different technique to scan the autocorrelation output buffer for the indication of a periodic signal which corresponds to heartbeat. For each examination, the digital signal processor 44 generates a candidate heart rate signal. For clarity, it should be noted that the block 148 implements the function of the signal processor 28 shown in FIG. 1. The function performed at block 148 is described in greater detail below in connection with FIG. 11.

At a block 150, the digital signal processor 44 performs the arbitration function by selecting one of the candidate heart rate signals generated at the block 148. This selection is performed in accordance with certain predetermined criteria, including reasonableness criteria. These criteria can include the elapsed time which the user has been operating the exercise appliance 58, the value of the RPM signal (which indicates the effort being expended by the user), and the value of the previously selected candidate heart rates. If none of the candidate heart rate signals is acceptable, then the value of a previously selected (and preferably, most recent) signal is used.

For example, candidate heart rates which are harmonics of previously selected heart rates are rejected. Thus, if a particular candidate heart rate is equal to the value of a previously selected heart rate divided or multiplied by a whole number, then that heart rate is rejected. Also if a particular candidate heart rate is equal to the RPM signal or a multiple thereof, then it is likely that the candidate heart rate is actually measuring the cycles of biopotential signals generated by the user's leg muscles as he pedals the bike at the rate indicated by the RPM signal. In such a case, that particular candidate heart rate is rejected. Similarly, if the previously selected heart rate is a very high heart rate, such as 150 beats per minute, and a candidate heart rate is a very low rate, such as 50 beats per minute, the candidate heart rate is rejected, because it is unlikely that the user's heart rate would decrease from 150 beats per minute to 50 beats per minute in one sample cycle.

By way of another example, if a candidate heart rate is outside of a predetermined range (preferably 50 to 200), it will be rejected because human beings typically have heart rates within known ranges. Thus, a candidate heart rate of 10 beats per minute is rejected because it is too low. By way of another example, heart rate should increase with elapsed time and the value of the RPM signal. Thus, over time, a decreasing candidate heart rate is rejected in favor of an increasing candidate heart rate, particularly where the value of the RPM signal is steady or increasing.

Computer routines may be used to implement the foregoing functions. The exact nature of these routines depends on the particular embodiment in which the invention is implemented. A computer routine which is used in the preferred embodiment by the digital signal processor 44 is discussed in more detail below.

At a block 152, the digital signal processor 44 writes a data packet to its serial port interface buffer (not shown). As discussed above, the microprocessor 40 via the serial port interface 46. As discussed above, the data packet sent to the microprocessor 40 comprises 8 bytes, including a byte containing the value of the selected candidate heart rate. It is this value which the microprocessor 40 transmits to display 54 and which is visible to the user.

Figure 11:
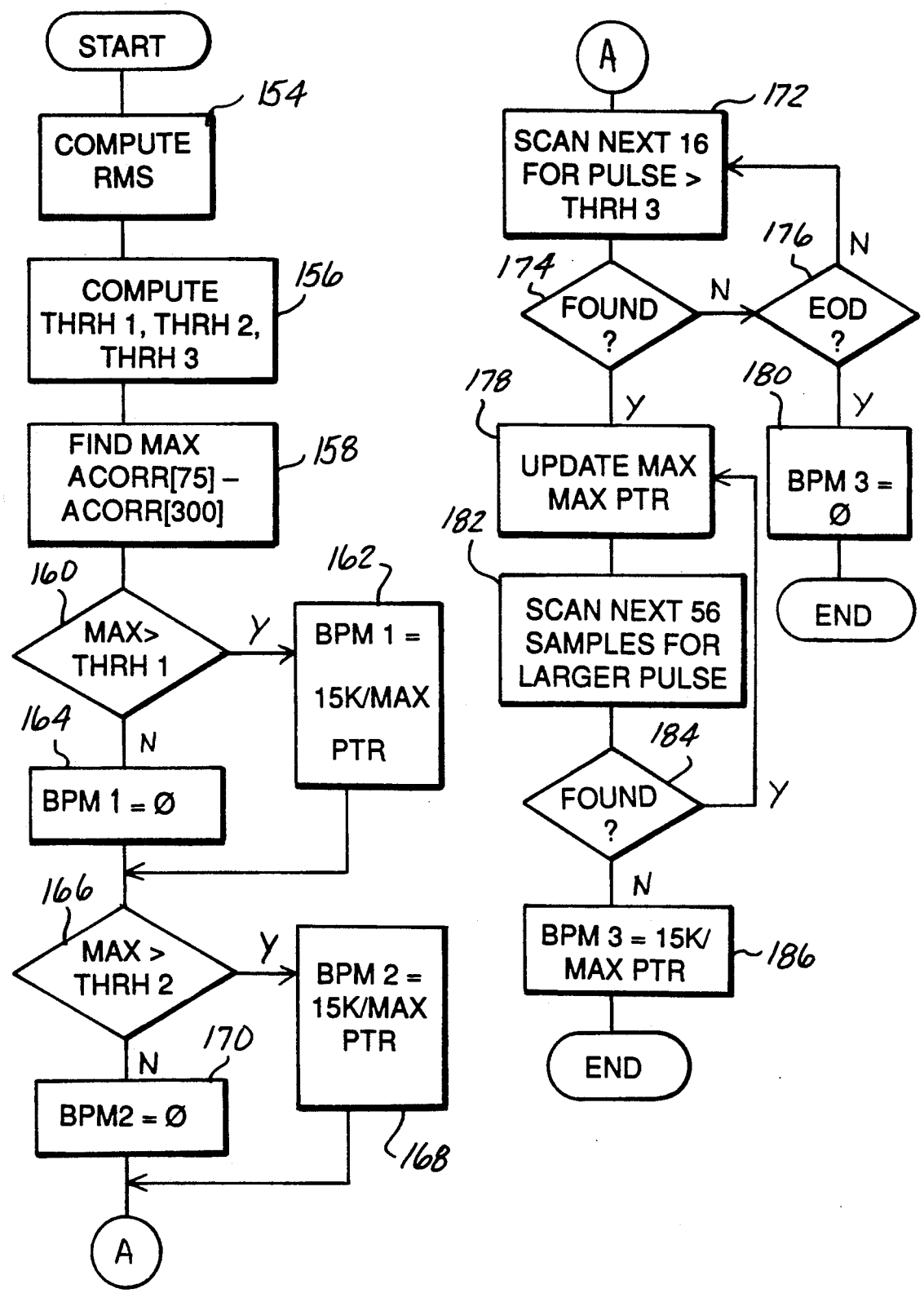
FIG. 11 is a logic flow chart illustrating the signal indication operation of the digital signal processor of the apparatus shown in FIG. 2.

Referring to FIG. 11, the operation of digital signal processor 44 at the block 148 is described in greater detail. At block 154 the digital signal processor computes the root-mean-square ("RMS") value of the autocorrelation output buffer. At block 156, three threshold values (THRH1, THRH2, and THRH3) are computed. The first threshold value (THRH1) is equal to the RMS value multiplied by a first constant (preferably one). The second threshold value (THRH2) is set equal to the RMS value multiplied by times a second constant (preferably equal to 1.25). The third threshold value (THRH3) is set equal to a percentage (preferably, 20%) of the largest value (typically the first element) of the autocorrelation output buffer.

At a block 158 the digital signal processor 44 searches for a peak value within a predetermined range of the autocorrelation output buffer. Preferably, this range is from the 75th element to the 300th element. At a decision block 160 this peak value is compared to the first threshold value (THRH1). If the peak value is greater than THRH1, control moves to a block 162. Otherwise control continues to a block 164 where the first candidate heart rate (BPM1) is set equal to zero. At the block 162 the first candidate heart rate (BPM1) is set equal to a constant divided by P, where P is the pointer to that element of the autocorrelation output buffer which contains the peak value found in the block 158. Preferably the constant equals the number of samples per minute. In the preferred embodiment, the analog output of the biopotential sensor 38 is sampled every four milliseconds by the microprocessor 40. Thus, 250 samples are taken each second, and 15,000 samples are taken each minute. In this case, the predetermined constant equals 15,000. For example, if at the block 158 a suitable peak value is found at the 100th element of the autocorrelation buffer array, the value of P is equal to 100. Accordingly, BPM1 is set equal to 15,000 divided by 100, or 150 beats per minute.

Upon completion of the block 162 (or the block 164, as the case may be), control moves to decision block 166. At the decision block 166, if the maximum value computed at the block 158 is greater than or equal to the second threshold value (THRH2), then control moves to a block 168. Otherwise control continues to a block 170. At the block 170 the second candidate heart rate (BPM2) is set to zero. At the block 168, the second candidate heart rate (BPM2) is set to a predetermined constant divided by P, as described above.

After completion of processing at the block 170 or 68 the program continues to block 172. At the block 172, the digital signal processor 44 begins scanning the autocorrelation output buffer for a pulse with a waveform which is characteristic of a heartbeat (a "characteristic pulse"). Such pulses are identified by pulse height, width and shape. The characteristic pulse shape is a local peak between, and in close proximity to, two local minimums. The characteristic pulse width is within a predetermined range (preferably, between 14 and 18 autocorrelation output buffer elements). The characteristic pulse height is greater than the third threshold value (THRH3). The concepts of pulse height and width is discussed below in connection with FIG. 13.

This scanning takes place within a predetermined range (or "data window") of the autocorrelation output buffer (preferably between the 75th and 300th elements). The buffer is scanned in blocks of predetermined size (preferably 16 buffer elements). Thus, in its first iteration, the digital signal processor 44 will search the 75th through 90th elements of the autocorrelation output buffer for a characteristic pulse. At decision block 174, if a characteristic pulse is not found, control moves to a decision block 176. Otherwise control continues to a block 178. At the block 176, if the digital signal processor 44 has reached the end of the data window, control moves to block 180, where the third candidate heart rate (BPM3) is set to zero and processing terminates. If the digital signal processor 44 has not reached the end of the data window, control returns to the block 172, where the digital signal processor 44 scans the next sixteen data elements for a characteristic pulse.

At the block 174, if a characteristic pulse has been located, then control moves to the block 178. It will be noted that the peak value of the located pulse will reside in an element of the autocorrelation output buffer. At the block 178, the index (or "pointer") to that element is stored in the variable P. For convenience, the value of pulse height is stored in the variable MAX. Thus, if the characteristic pulse has a pulse height of 4.25 and its peak is located at the 100th element of the output buffer, than P is set to the value 100 and MAX is set to the value 4.25.

Control then moves to a block 182 where the digital signal processor 44 scans the next 56 elements past the $P^{th}$ element, searching for a characteristic pulse which has a larger pulse height than the pulse height currently saved in MAX. At decision block 184, if such a larger pulse is found, then control returns to the block 178. At the block 178, the values of P and MAX are updated with the pointer and pulse height, respectively, of the newly-found pulse, and the scanning process at the block 182 is repeated. Otherwise control continues to the block 186, where the third candidate heart rate (BPM3) is set equal to a predetermined constant divided by P. Preferably, the predetermined constant equals the number of samples per minute. With respect to the arbitration function described above, the third candidate heart rate (BPM3) is generally more reliable than the first and second candidate heart rates (BPMI and BPM2, respective), and should be selected in the event that all other reasonableness criteria do not lead to a successful arbitration.

Figure 12:
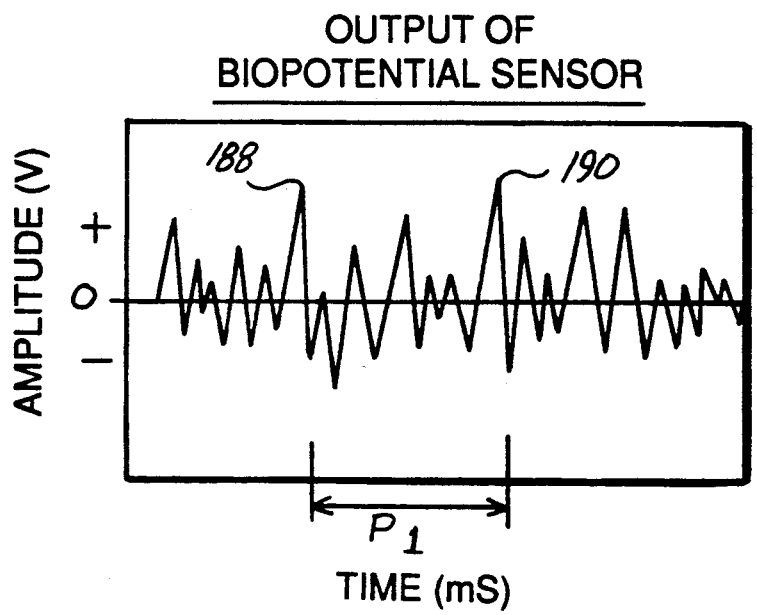
FIG. 12 is graph of the output in volts of the biopotential sensor shown in FIG. 5, as measured against time in milliseconds.
Figure 13:
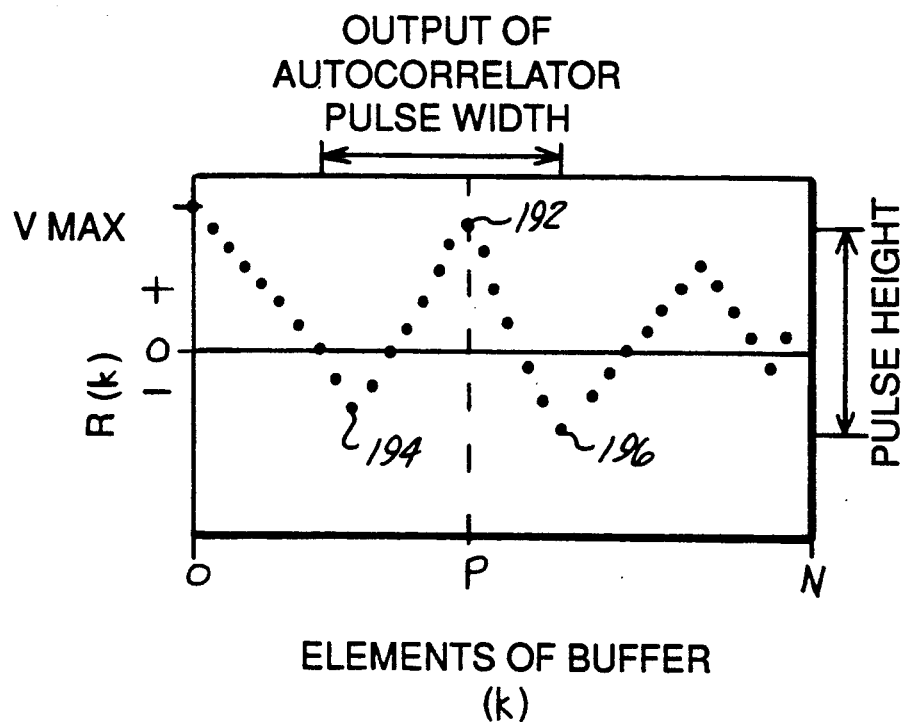
FIG. 13 is a graph of the digital output of the autocorrelation performed by the digital signal processor of the apparatus shown in FIG. 2.

Understanding of the operation of the invention is enhanced by reference to FIGS. 12 and 13. FIG. 12 is a graph of the output of the biopotential sensor 38 over time, measured in volts. As described above, this output is periodically digitized and sampled by the microprocessor 40 in cooperation with the A/D converter 42. As FIG. 12 illustrates, the output of the biopotential sensor 38 is a noisy signal with peaks shown at 188 and 190. For the purposes of this illustration, it is assumed that the peaks 188 and 190 are each indicative of a heartbeat of the user. Under this assumption, the heart rate is inversely proportional the time period P between the peaks 188 and 190.

After the output of the biopotential sensor 38 is digitized and sampled, it is read by digital signal processor 44 via the serial interface 46 as described above. As described above, digital signal processor 44 performs an autocorrelation at the block 146 on the digitized signal.

FIG. 13 is a graph of the results of this autocorrelation. As discussed above, the autocorrelation output is stored in a buffer array. In the graph depicted in FIG. 13, the horizontal axis shows k, the pointer to each element in the autocorrelation output buffer. The vertical axis shows $R_k$, the value contained in the $k^{th}$ element of the autocorrelation output buffer. Of general interest is the fact that, mathematically speaking, k is also the displacement (measured in samples) used in the autocorrelation to compute $R_k$.

As the graph indicates, the largest value of $R_k$ is found in the first element of the autocorrelation output buffer. However, a local peak 192 and local minimums 194 and 196 also exist. For purposes of this illustration it is assumed that the waveform characterized by the local peak 192 and local minimums 194 and 196 is characteristic of the user's heartbeat. In this case, pulse width is equal to the horizontal distance between the local minimums 194 and 196, as indicated in FIG. 13. Pulse height is the vertical distance between the local peak 192 and the local minimums 194 and 196. It will be observed that the local peak 192 is contained in the $P^{th}$ element of the autocorrelation output. As described above in connection with FIG. 11, the digital signal processor 44 computes the third candidate heart rate (BPM3) by dividing a predetermined constant (preferably, 15,000) by P, the pointer to the local peak 192.

Referring to FIG. 10, discussed above, the arbitration function at the block 150 is performed by the digital signal processor 44. Table One sets forth pseudocode illustrating computer routine used by the digital signal processor 44 in the preferred embodiment to perform the arbitration function.

Operating in accordance with the illustrated routine, the digital signal processor 44 selects one of the candidate heart rate signals BPM1, BPM2 and BPM3 generated by the digital signal processor 44 at the block 148. The value of the selected signal is stored in a variable ARB. The value of the five most recent previously selected signals are stored in an array ARB[0:4], with the most recent result being stored in the array storage element ARB[0]. The notation "approx=" as used in Table One means "equal within 5 beats per minute."

TABLE 1

```
Case 0:  number of past samples is < = 4
             arb = bpm3;
Case 1:  bpm1 = bpm2 = bpm3
         if bpm3 within 25 of arb[0], then
             arb = bpm3;
         else if (bpm3 not within 25 of arb[0]) and (arb[0]
                 within 15 of arb[1]), then
             if bpm3 within 6 of arb[0]*2, then
                 arb = bpm3;
             else if arb[0] < > any one of other arb array
                 elements, then
                 arb = arb[0]
             else if bpm3 not within 25 of any element of
                 arb array then,
                 arb = arb[0];
             else arb = bpm3;
         else if (bmp3 not within 25 of arb[0]) and (arb[0]
                 not within 15 of arb[1]), then
             if arb[0]* 2 within 6 of bpm 3, then
                 arb = bmp3
             else if (arb[1] approx = bpm3) and
                 (arb[2] approx = bpm3), then
                 arb = bpm3;
             else arb = arb[0];
         else if 2*bpm3 approx = arb[0], then arb = 2*bpm3;
         else arb = bpm3;
Case 2:  (bpm1 = bpm2) and (bpm1 < > bpm3) and (bpm3 < > 0)
         if bpm1 * 2 = bpm3, then arb = bpm3;
         else if bpm3 / 2 = arb[0], then arb = bpm1;
         else if 2 * bpm1 = arb [0], then arb = 2 * bpm1;
         else if bpm1 / 3 approx = bpm3, then arb = bpm3;
         else if 2 * bpm3 approx = bpm1, then
             if bpm3 approx = arb[0], then
                 arb = bpm3;
             else arb = bpm1};
         else if bpm3 approx = arb[0], then arb = bpm3;
         else if (bpm1 > bpm3) and (bpm1 > arb[0]) and
                 (arb[0] > bpm3), then
             if (bpm1 - arb[0] < 20), then arb = bpm1;
             else arb = arb[0]};
         else if (bpm1 - arb[0] < = 20) and
                 (arb[0] -bpm3 > 20), then
             arb = bpm1;
         else if (2*bpm3 = arb[0]), then arb = 2*bpm3;
         else if (bpm3 > bpm1) and (bpm3 > = arb[0]) and
                 (arb[0] > bpm1), then
             if (bpm1 approx = arb[0] and (bpm3 - bpm1 >
                 10), then
                 arb = bpm1;
             else if (bpm3 - arb[0] < 20), then arb = bpm3
             else arb = arb[0];
         else if (bpm3 > bpm1) and (bpm3 > arb[0]) and
                 (arb[0] > bpm1), then
             if (arb[0] - bpm3 < 20), then arb = bpm3;
             else arb = arb[0];
         else if (bpm1 - bpm3 < = 4), then arb = bpm3;
         else if (arb[0] not = 0) and (arb[1] not = 0), then
             arb = arb[0];
         else arb = 0;
Case 3:  (bpm1 = bpm2) and (bpm3 = 0)
```

TABLE 1-continued

```
        if (arb[0] not = 0) and (bpm1 - arb[0] > 24), then
            if (bpm1 / 2 - arb[0] < = 20) and
                (bpm1 > 100), then arb = bpm1 / 2;
            else if (bpm1 / 2 - arb[0] < = 20) and
                bpm1 < = 100, then arb = bpm1;
            else if (bpm1 approx = arb[1]) and (bpm1
                approx = arb[1]). then arb = bpm1;
            else arb = arb[0]};
        else arb = bpm1;
Case 4:  (bpm1 not = bpm2) and (bpm1 not = bpm3)
            arb = arb[0];
Case 5:  (bpm1 = bpm3) and (bpm1 not = bpm2)
         if (bpm3 approx = arb[0]), then arb = bpm3;
         else arb = arb[0];
Case 6:  (bpm2 = bpm3) and (bpm1 not = bpm2)
         if (bpm3 = arb[0]), then arb = bpm3;
         else arb = arb[0];
Case 7:  All other cases
         arb = 0;
         -------- END OF TABLE ONE --------
```

In the illustrated routine, the selected signal is chosen on the basis of the previously selected signals, the values of which are contained in the ARB array. The criteria utilized were developed through experimentation, and may vary in different embodiments of the invention. No external data is utilized in the illustrated routine, although the present invention provides for the use of external data, as discussed above.

As indicated, the illustrated routine utilizes six groups of selection criteria, designated as Case 1 through Case 6. In each group one of the three candidate heart rate signals BPM1, BPM2 and BPM3, or one of the previously selected heart rate signals, is selected as the current heart rate signal, and is placed in the variable ARB. If no suitable heart rate signal is present, the value of ARB is set to zero.

We claim:

1. An apparatus for measuring heart rate, comprising:
    an exercise apparatus:
    sensor means associated with said exercise apparatus for generating an input signal including the biopotential signal produced by the heart of the user while exercising;
    autocorrelating means responsive to said input signal for periodically generating an autocorrelation signal of said input signal over a predetermined time period; and
    signal indication means responsive to said autocorrelation signal for detecting the presence of a periodic signal in said autocorrelation signal and generating a heart rate signal corresponding to the frequency of said periodic signal.

2. The apparatus according to claim 1 wherein said signal indication means includes:
    means for detecting a peak in said autocorrelation signal, which peak is in excess of a first threshold value;
    means for detecting a peak in said autocorrelation signal, which peak is in excess of a second threshold value; and
    wherein said first threshold value is equal to the root-mean-square value fo said autocorrelation signal, and wherein said second threshold value is equal to said root-mean-squared value times a predetermined constant which is greater than one.

3. The apparatus according to claim 1 wherein said signal indication means includes means for detecting a pulse which has at least two waveform characteristics that are associated with heartbeat.

4. The apparatus according to claim 1 wherein said waveform caracteristic is pulse shape.

5. An apparatus for measuring heart rate, comprising:
    an exercise apparatus for providing a user with exercise;
    sensor means associated with said exercise apparatus for generating an input signal including the biopotential signal produced by the heart of the user while exercising;
    autocorrelating means responsive to said input signal for periodically generating an autocorrelation signal of said input signal over a predetermined time period;
    signal processing means responsive to said autocorrelation signal for detecting a plurality of indications of periodic signals in said input signal, and generating a plurality of candidate signals, each corresponding to one of the detected indications; and
    arbitration means responsive to said output signals for selecting according to predetermined selection criteria that one of said output signals which is most likely a true heart rate.

6. The apparatus according to claim 5 wherein one of said signal indications is the presence of a waveform that is characteristic of a heartbeat.

7. The apparatus according to claim 5 wherein said signal processing means generates first and second candidate signals;
    said first candidate signal corresponding to a peak in said autocorrelation signal that is in excess of a first threshold value; and
    said second candidate signal corresponding to a peak in said autocorrelation signal that is in excess of a second threshold value.

8. The apparatus according to claim 5 wherein said predetermined selection criteria include reasonableness criteria.

9. The apparatus according to claim 8 wherein said arbitration means further includes means for storing the value of the selected candidate signal; and wherein said reasonableness criteria include rejecting one of said plurality of candidate signals if it deviates from the previously selected candidate signal by more than a predetermined amount.

10. The apparatus according to claim 8 wherein said arbitration means further includes means for detecting the amount of work being performed by the user, and said reasonableness criteria include rejecting one of said candidate signals if the value of said candidate signal is not proportional to the amount of work being performed by the user.

11. The apparatus according to claim 8 wherein said reasonableness criteria include rejecting one of said candidate signals if the value of said candidate signal falls outside of a predetermined range.

12. The apparatus according to claim 11 wherein said arbitration means further comprises means for detecting the rate at which work is being performed by the user, and said predetermined range is a function of said rate.

13. An apparatus for measuring heart rate of a user while exercising, comprising:
   sensor means for generating an input signal including the biopotential signal produced by the user's heart;
   autocorrelating means responsive to said input signal for periodically generating an autocorrelation signal of said input signal over a predetermined time period;
   signal processing means responsive to said autocorrelation signal for detecting a plurality of indications of periodic signals in said autocorrelation signal and generating a plurality of candidate signals corresponding to each of the detected indications; and
   arbitration means responsive to said output signals for selecting according to predetermined criteria that one of said candidate signals which most likely represents true heart rate.

14. The apparatus according to claim 13 further comprising analog-to-digital conversion means responsive to said input signal for generating a digital signal corresponding to said input signal, wherein said autocorrelating means is responsive to said digital signal.

15. The apparatus according to claim 14 wherein said autocorrelating means is a programmable digital computer.

16. The apparatus according to claim 15 further comprising a low pass digital filter responsive to said digital signal, wherein said autocorrelating means is responsive to the output of said digital filter.

17. The apparatus according to claim 13 wherein said autocorrelating means generates said autocorrelation signal in the time domain.

18. The apparatus according to claim 13 further comprising an adjustable gain amplifier for amplifying said input signal, and means for adjusting gain of said adjustable gain amplifier so that output of said adjustable gain amplifier remains within predetermined upper and lower limits.

19. The apparatus according to claim 13 wherein one of said plurality of signal indications is the presence of a waveform having a pulse length, width and shape that is characteristic of a heartbeat.

20. The apparatus according to claim 19 wherein said signal processing means generates first and second candidate signals:
   said first candidate signal corresponding to a peak in said autocorrelation signal that is in excess of a first threshold value; and
   said second candidate signal corresponding to a peak in said autocorrelation signal that is in excess of a second threshold value.

21. The apparatus according to claim 20 wherein said signal processing means is a programmable digital computer.

22. The apparatus according to claim 13 wherein said sensor means further comprises a plurality of electrodes for sensing the biopotential signal produced by the user's body when said electrodes are placed into physical contact with the user.

23. The apparatus according to claim 22 wherein said sensor means further comprise means responsive to said electrodes for generating a heands on/off signal which indicates whether said electrodes are in contact with the user.

24. The apparatus according to claim 23 wherein said input signal is set to zero if said hands on/off signal indicates that said electrodes are not touching the human.

25. The apparatus according to claim 24 wherein said autocorrelating means is responsive to said hands on/off signal and discontinues processing said input signal if hands on/off signal indicates that the electrodes are not touching the user for a predetermined amount of time, and does not resume processing said input signal until said hands on/off signal indicates that the electrodes are touching the user.

26. The apparatus according to claim 13 wherein said predetermined criteria include reasonableness criteria.

27. The apparatus according to claim 26 further comprising means for generating a motion signal which is the frequency of repetitive cycles of motion performed by the user while exercising, and wherein said reasonableness criteria include rejecting one of said output signals if its value is a multiple of the value of said motion signal.

* * * * *

UNITED STATES PATENT AND TRADEMARK OFFICE
CERTIFICATE OF CORRECTION

PATENT NO.  : 5,243,993

DATED       : September 14, 1993

INVENTOR(S) : Donald J. Alexander et al.

It is certified that error appears in the above-identified patent and that said Letters Patent is hereby corrected as shown below: On the title page: Item [56]

Under "References Cited" "McKown et al." should read --McKnown et al.--

Col. 4, line 54, delete "Soeech" and insert --Speech--

Col. 5, line 5, delete "tho" and insert --the--

Col. 5, line 16, delete "Confiquration" and insert --Configuration--

Col. 5, line 19, after "FIG. 1" insert a period (.)

Col. 5, line 19, delete "inoludes" and insert --includes--

Col. 6, line 7, after "A-A'" insert a period (.)

Col. 7, line 12, delete "Confiouration" and insert --Configuration--

Col. 7, line 64, delete "(startOof-data flag)" and insert therefor --(start-of-data flag)--

Col. 9, line 51, delete "accordinq" and insert --according--

Col. 9, line 52, delete "followinq" and insert --following-- (Specification page 16, line 22).

Col. 11, line 34, delete "loO" and insert --100--

Col. 12, line 39, delete "BPMI" and insert --BPM1--

UNITED STATES PATENT AND TRADEMARK OFFICE
CERTIFICATE OF CORRECTION

PATENT NO. : 5,243,993
DATED : September 14, 1993
INVENTOR(S) : Donald J. Alexander et al.

It is certified that error appears in the above-identified patent and that said Letters Patent is hereby corrected as shown below:

Col. 12, line 54, after "period" delete "P" and insert --$P_1$-- (Application page 22, line 2).

Col. 15, line 62, delete "fo" and insert --of--

Col. 16, line 24, delete "caracteristic" and insert --characteristic--

Col. 18, line 26, delete "heands" and insert --hands--

Signed and Sealed this

Twenty-second Day of March, 1994

Attest:

BRUCE LEHMAN

Attesting Officer     Commissioner of Patents and Trademarks